United States Patent [19]
Goodby et al.

[11] Patent Number: 5,798,058
[45] Date of Patent: Aug. 25, 1998

[54] LIQUID CRYSTAL COMPOUNDS, MIXTURES AND DEVICES

[75] Inventors: John William Goodby; Kenneth Johnson Toyne; Michael Hird; Robert Andrew Lewis, all of Hull, United Kingdom

[73] Assignee: Secretary of State for Defence in her Britannic Majesty's Government of the United Kingdom of Gt. Britain & N. Ireland of Defence Evaluation and Research Agency, United Kingdom

[21] Appl. No.: 765,351

[22] PCT Filed: Jun. 30, 1995

[86] PCT No.: PCT/GB95/01525

§ 371 Date: Dec. 31, 1996

§ 102(e) Date: Dec. 31, 1996

[87] PCT Pub. No.: WO96/01246

PCT Pub. Date: Jan. 18, 1996

[30] Foreign Application Priority Data

Jul. 1, 1994 [GB] United Kingdom ............... 9413324

[51] Int. Cl.$^6$ .................. C09K 19/34; C09K 19/12; C09K 19/30; C07C 69/76
[52] U.S. Cl. .................. 252/299.61; 252/299.63; 252/299.66; 560/65
[58] Field of Search .............. 252/299.61, 299.63, 252/299.66; 560/65

[56] References Cited

U.S. PATENT DOCUMENTS

| | | | |
|---|---|---|---|
| 5,032,314 | 7/1991 | Ushioda et al. | 252/299.65 |
| 5,139,697 | 8/1992 | Togano et al. | 252/299.61 |
| 5,186,858 | 2/1993 | Terada et al. | 252/299.61 |
| 5,217,644 | 6/1993 | Nohira et al. | 252/299.6 |
| 5,236,620 | 8/1993 | Reiffenrath et al. | 252/299.61 |
| 5,248,447 | 9/1993 | Reiffenrath et al. | 252/299.63 |
| 5,250,219 | 10/1993 | Mori et al. | 252/299.61 |
| 5,273,680 | 12/1993 | Gray et al. | 252/299.66 |
| 5,393,459 | 2/1995 | Wachtler et al. | 252/299.63 |
| 5,439,613 | 8/1995 | Takeshita et al. | 252/299.66 |
| 5,512,208 | 4/1996 | Terada et al. | 252/299.6 |
| 5,580,489 | 12/1996 | Shinjo et al. | 252/299.63 |
| 5,599,479 | 2/1997 | Shinjo et al. | 252/299.61 |

FOREIGN PATENT DOCUMENTS

| | | |
|---|---|---|
| A0343487 | 11/1989 | European Pat. Off. . |
| A0401522 | 12/1990 | European Pat. Off. . |
| A0501849 | 9/1992 | European Pat. Off. . |
| 2216523 | 3/1989 | United Kingdom . |
| 2249309 | 9/1991 | United Kingdom . |
| WP89/08687 | 9/1989 | WIPO . |

OTHER PUBLICATIONS

Liquid Crystals, vol. 16, No. 4, Apr. 1994, London, GB, pp. 625–641, Michael Hird "The synthesis and transition temperatures of some ferroelectric host materials based on 4-and 4'(trans-4-alkylcyclohexylmethoxy)-2,3-difluorobiphenyls".

*Primary Examiner*—C H Kelly
*Attorney, Agent, or Firm*—Nixon & Vanderhye

[57] ABSTRACT

Compounds of formula (I) which are suitable for use in liquid crystal devices including those devices which exploit the electroclinic effect. The compounds of formula (I) may also be used as chiral dopants suitable for use with ferroelectric liquid crystals or they may be used as chiral nematic dopants. The compounds of formula (I) may be used in mixtures suitable for use in devices

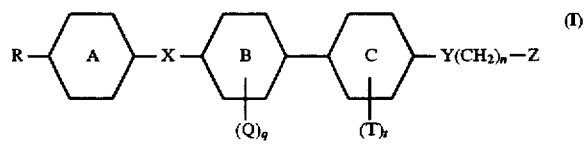

17 Claims, 7 Drawing Sheets

LIQUID CRYSTAL COMPOUNDS, MIXTURES AND DEVICES

This application is a 35 U.S.C. 371 of PCT/GB95/01525 filed Jun. 30, 1995.

This invention relates to novel compounds suitable for use in liquid crystal mixtures and their inclusion in liquid crystal devices.

Liquid crystals can exist in various phases. In essence there are three different classes of liquid crystalline material, each possessing a characteristic molecular arrangement. These classes are nematic, cholesteric and smectic. A wide range of smectic phases exists, for example smectic A and smectic C. Some liquid crystal materials possess a number of liquid crystal phases on varying the temperature, others have just one phase. For example, a liquid crystal material may show the following phases on being cooled from the isotropic phase:- isotropic - nematic - smectic A - smectic C - solid. If a material is described as being smectic A then it means that the material possesses a smectic A phase over a useful working temperature range.

Materials possessing a smectic A ($S_A$) phase may exhibit an electroclinic effect. The electroclinic effect was first described by S. Garoff and R. Meyer, Phys. Rev. Lett., 38, 848 (1977). An electroclinic device has also been described in UK patent application GB 2 244 566 A. This particular device helps to overcome the poor alignment problems of electroclinic (EC) devices using a surface alignment that gives a surface tilt within a small range of angles. When a smectic A phase is composed of chiral molecules, it may exhibit an electroclinic effect, ie a direct coupling of molecular tilt to applied field. The origin of the electroclinic effect in a smectic A phase composed of chiral polar molecules has been described by Garoff and Meyer as follows. The application of an electric field parallel to the smectic layers of such a smectic A phase biases the free rotation of the transverse molecular dipoles and therefore produces a non-zero average of the transverse component of the molecular polarization. When such a dipole moment is present and coupled to the molecular chirality, a tilt of the long molecular axis (the director) is induced in a plane perpendicular to the dipole moment.

In thin samples for example 1-3 µm and with the smectic layers tilted or perpendicular with respect to the glass plates the electroclinic effect is detectable at low applied fields.

In an aligned smectic A sample a tilt of the director is directly related to a tilt of the optic axis. The electroclinic effect results in a linear electro-optic response. The electro-optic effect can manifest itself as a modulation of the effective birefringence of the device.

Electroclinic (EC) devices are useful, for example, in spatial light modulators having an output that varies linearly with applied voltage. A further advantage of EC devices is that they have high speed response times, much faster than twisted nematic type devices. One known type of ferroelectric device is bistable, in contrast the EC device is not bistable and has an output that varies linearly with applied voltage.

The electroclinic effect is sometimes referred to as the soft-mode effect see G. Andersson et al in Appl. Phys. Lett., 51, 9, (1987). In general terms, regarding the electroclinic effect, it is advantageous if on applying a small voltage there results a large induced tilt. An increase in induced tilt may result in an increase in contrast ratio. It is also advantageous if a large induced tilt can be obtained at as low a voltage as possible.

It is also advantageous if the relationship between molecular induced tilt and applied voltage is temperature independent. When an increase in applied voltage results in little or no change in induced tilt then the material being tested is generally referred to as exhibiting a saturation voltage effect.

By $S_A^*$ is meant a $S_A$ phase which contains some proportion of chiral molecules.

Documents EP-A-0401522, EP-A-0501849, EP-A-0343487 and Liquid Crystals, 1994, vol. 16(4), 625-641 are concerned with liquid crystal materials containing a cyclohexyl group. Cholesteric or chiral nematic liquid crystals possess a twisted helical structure which is capable of responding to a temperature change through a change in the helical pitch length. Therefore as the temperature is changed then the wavelength of the light reflected from the planar cholesteric structure will change and if the reflected light covers the visible range then distinct changes in colour occur as the temperature varies. This means that there are many possible applications including the areas of thermography and thermooptrics.

The cholesteric mesophase differs from the nematic phase in that in the cholesteric phase the director is not constant in space but undergoes a helical distortion. The pitchlength for the helix is a measure of the distance for the director to turn through 360°.

By definition a cholesteric material is a chiral material. Cholesteric materials may also be used in electrooptical displays as dopants, for example in twisted nematic displays where they may be used to remove reverse twist defects, they may also be used in cholesteric to nematic dyed phase change displays where they may be used to enhance contrast by preventing wave-guiding.

Thermochromic applications of cholesteric liquid crystal materials usually use thin-film preparations of the cholesterogen which are then viewed against a black background. These temperature sensing devices may be placed into a number of applications involving thermometry, medical thermography, non-destructive testing, radiation sensing and for decorative purposes. Examples of these may be found in D. G. McDonnell in Thermotropic Liquid Crystals, Critical Reports on Applied Chemistry, Vol. 22, edited by G. W. Gray, 1987 pp 120–44; this reference also contains a general description of thermochromic cholesteric liquid crystals. Generally, commercial thermochromic applications require the formulation of mixtures which possess low melting points, short pitch lengths and smectic transitions just below the required temperature-sensing region. Preferably the mixture or material should retain a low melting point and high smectic - cholesteric transition temperatures.

In general, thermochromic liquid crystal devices have a thin film of cholesterogen sandwiched between a transparent supporting substrate and a black absorbing layer. One of the fabrication methods involves producing an 'ink' with the liquid crystal by encapsulating it in a polymer and using printing technologies to apply it to the supporting substrate. Methods of manufacturing the inks include gelatin microencapsulation, U.S. Pat. No. 3,585,318 and polymer dispersion, U.S. Pat. Nos. 1,161,039 and 3,872,050. One of the ways for preparing well-aligned thin-film structures of cholesteric liquid crystals involves laminating the liquid crystal between two embossed plastic sheets. This technique is described in UK patent 2,143,323. According to this invention materials are provided of Formula I:

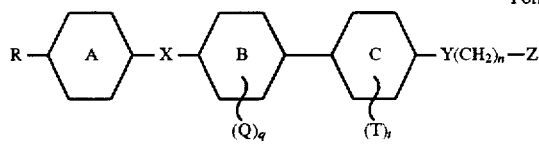

Formula I wherein

R may be $C_{1-12}$ straight or branched chain alkyl or alkenyl;

A is cyclohexyl;

X is $CH_2CH_2$, $CH_2O$, or $OCH_2$;

Q and T are independently chosen from fluorine or chlorine and q and t are independently chosen from 0, 1 or 2;

B and C are independently chosen from pyridine, pyrimidine, phenyl;

Y is O, $CO_2$, OCO or a single bond;

n may be 0–5;

Z is given by Formula II and possesses a chiral centre:

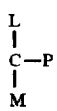

Formula II wherein L may be $C_{1-5}$ alkyl or alkenyl, H, F, CN, $CF_3$, $CHF_2$, $CH_2F$;

M is $C_{1-5}$ alkyl or alkenyl, or H;

P may be H or the group $R_2$ wherein $R_2$ contains from 1–12 carbon atoms and may contain a double bond or P may be $CO_2R_3$ where $R_3$ may be $C_{1-5}$ alkyl;

provided that there is at least one phenyl ring present substituted with at least one fluorine or chlorine.

Preferably R is $C_{3-8}$ straight chain alkyl;

Preferably X is $CH_2CH_2$;

Preferably B is phenyl;

Preferably Q (if present) is F;

Preferably C is pyrimidine or phenyl;

Preferably T (if present) is F;

Preferably Y is O or $CO_2$;

Preferably n=0–2;

Preferably M=H;

Preferably L=Me or F;

Preferably P is $CO_2Et$ or $CH_2CH_2CHC(CH_3)_2$ or $C_3$–$C_8$ alkyl chain.

The invention will now be described, by way of example only, with reference to the following diagrams.

Figure 1:
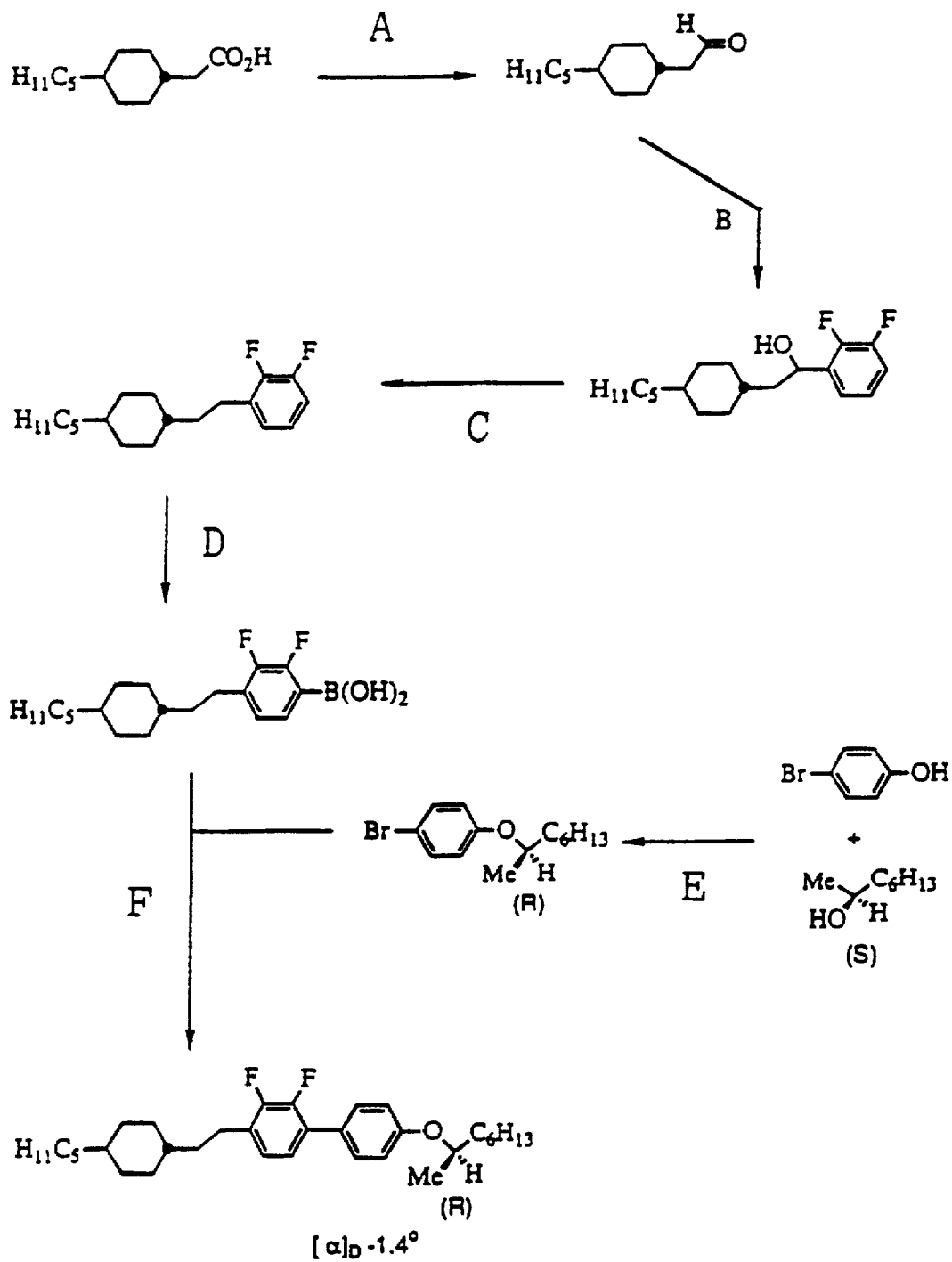
FIGS. 1–6 show synthetic schemes for the preparation of compounds.

Reagents used in the synthetic route of FIG. 1 are shown in the corresponding Scheme 1:

A: $LiAl(O^tBu)_3H$, DMF, $(COCl)_2$, MeCN, THF.

B: BuLi, 1,2-difluorobenzene.

C: PTSA, toluene; $H_2$, Pd/C.

D: BuLi; $B(O^iPr)_3$; HCl.

E: $PPh_3$, DEAD, THF.

F: $Pd(PPh_3)_4$, 2M $Na_2CO_3$, monoglyme.

where:

DEAD=diethyl azodicarboxylate.

THF=tetrahydrofuran.

PTSA=toluene-p-sulphonic acid.

Figure 2:
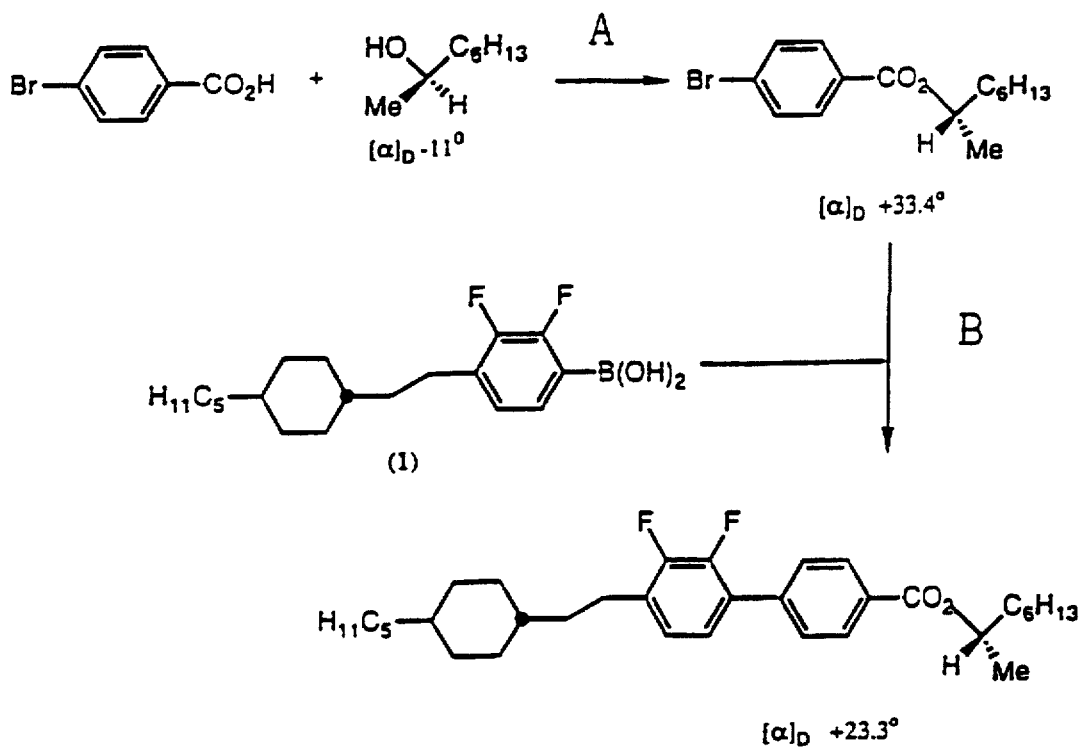

Reagents used in the synthetic route of FIG. 2 are shown in the corresponding Scheme 2:

A: DEAD, $PPh_3$.

B: $Pd(PPh_3)_4$.

Figure 3:
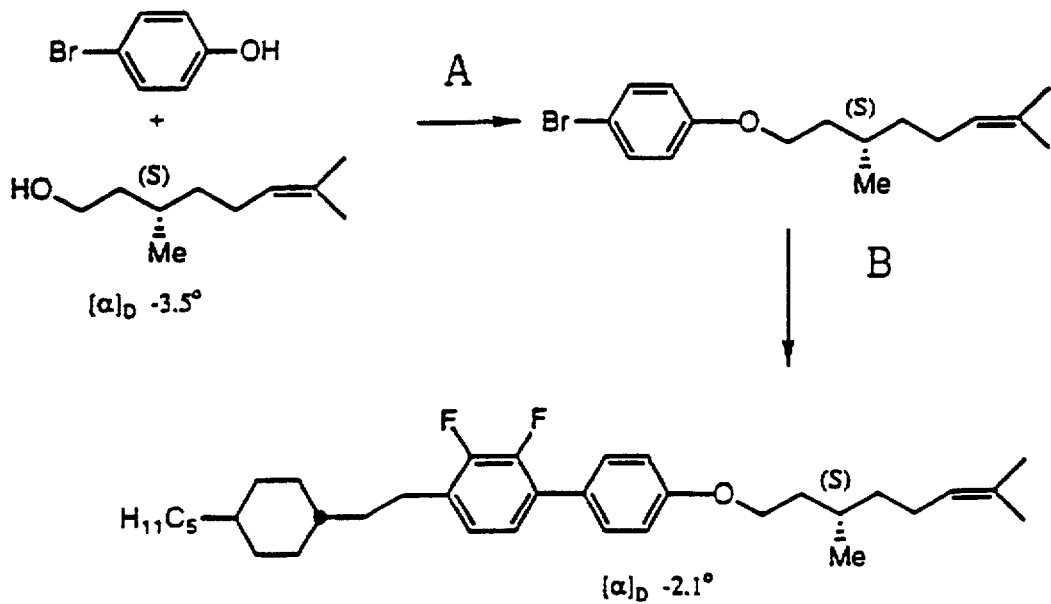

Reagents used in the synthetic route of FIG. 3 are shown in the corresponding Scheme 3:

A: DEAD, $PPh_3$.

B: $Pd(PPh_3)_4$+ compound 1 from FIG. 2

Figure 4:
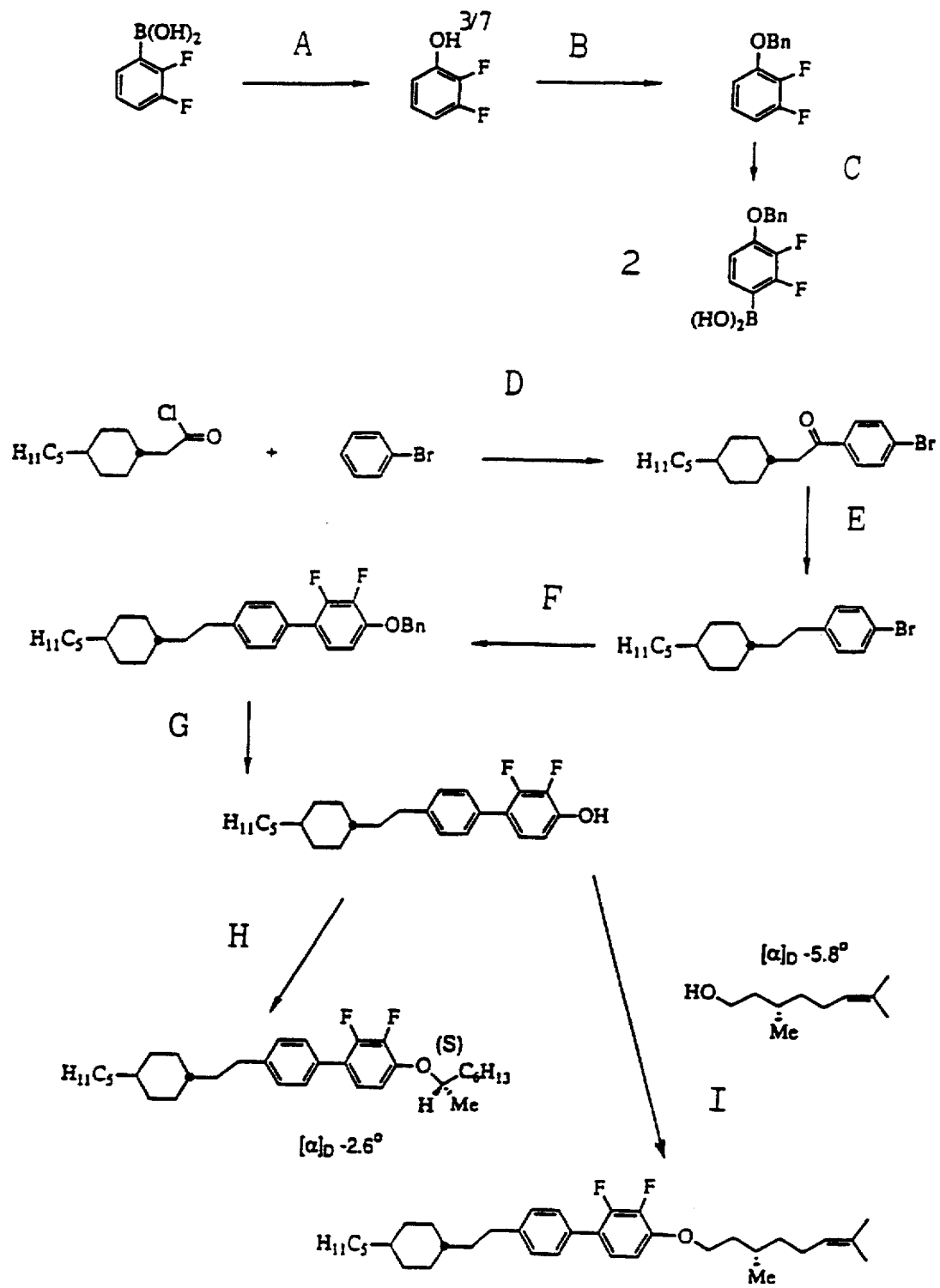

Reagents used in the synthetic route of FIG. 4 are shown in the corresponding Scheme 4:

A: $H_2O_2$, ether.

B: $K_2CO_3$, BnBr, butanone.

C: BuLi, $B(OMe)_3$, HCl.

D: $AlCl_3$.

E: $Et_3SiH$, TFA.

F: (2) from FIG. 4, catalyst, Pd[O].

G: $H_2$, Pd/C.

H: (R)-(–)-2-octanol, DEAD, $PPh_3$.

I: $PPh_3$, DEAD.

TFA=trifluoroacetic acid.

Figure 5:
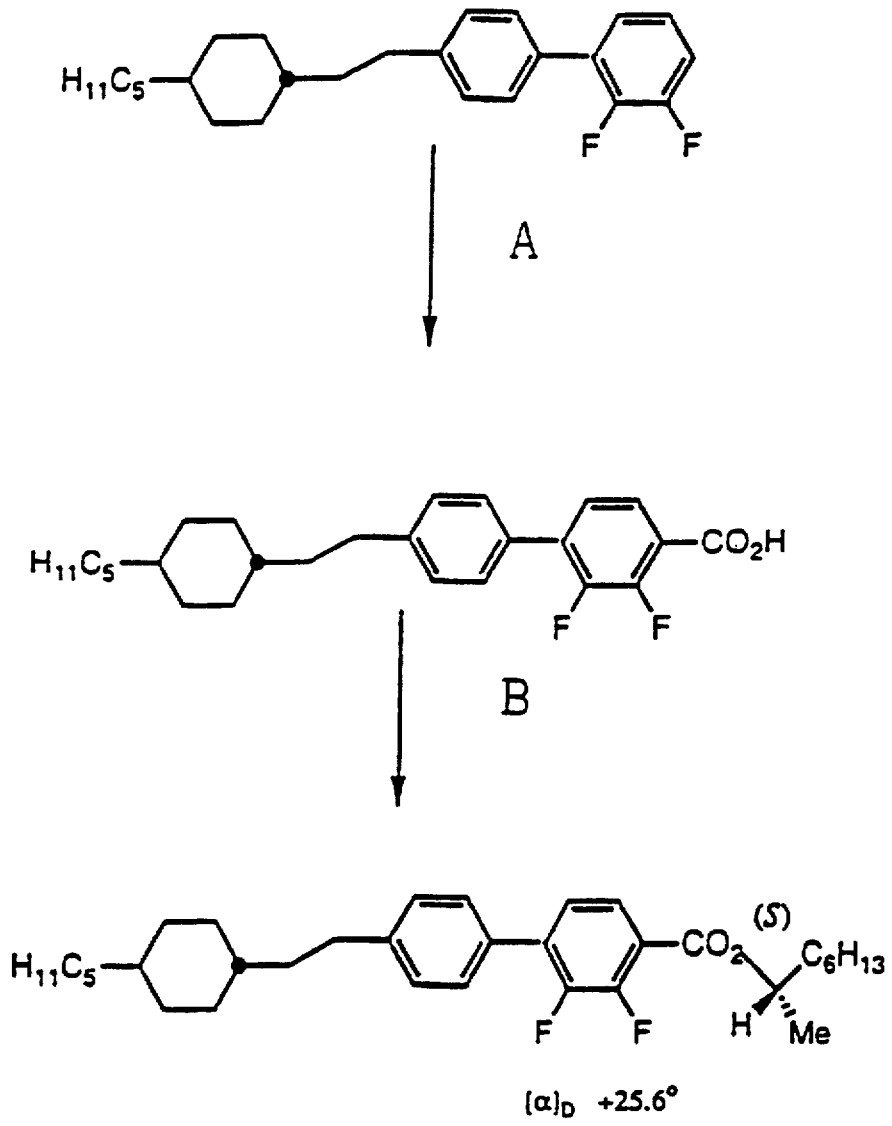

Reagents used in the synthetic route of FIG. 5 are shown in the corresponding Scheme 5:

A: BuLi, $CO_2$.

B: (R)-(–)-2-octanol, $PPh_3$, DEAD.

Figure 6:
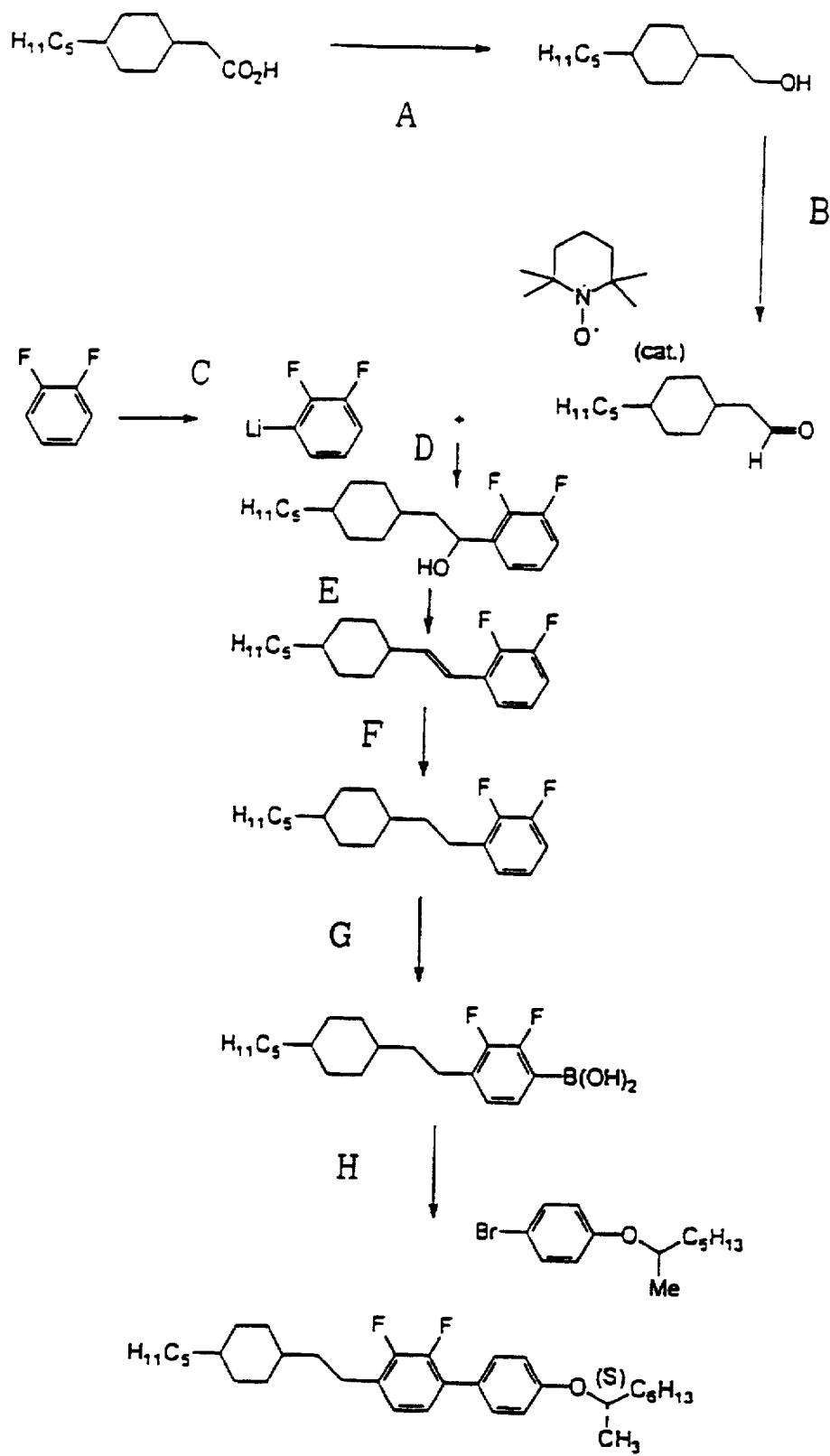

FIG. 1 shows the reaction scheme for the preparation of the (R) enantiomer for Example 1. FIG. 6 shows a reaction scheme for the preparation of the corresponding (S) enantiomer. In FIG. 1 the aldehyde was prepared by selective reduction of the acid. In FIG. 6 the acid was first reduced to the alcohol and then oxidised to the aldehyde using bleach and a nitroxyl radical.

Reagents used in the synthetic route of FIG. 6 are shown in the corresponding Scheme 6:

A: $LiAlH_4$, THF.

B: $CH_2Cl_2$, pH9.5, NaOCl, KBr(cat).

C: BuLi –65° C.

D: in situ with product from step C, then aqueous $NH_4Cl$.

E: p-toluenesulphonic acid, toluene, reflux (Dean/Stark).

F: $H_2$, Pd/C, EtOAc.

G: BuLi, $B(OMe)_3$, HCl.

H: $Pd(PPh_3)_4$, 2M $Na_2CO_3$, 1,2-dimethoxyethane.

Figure 7A:
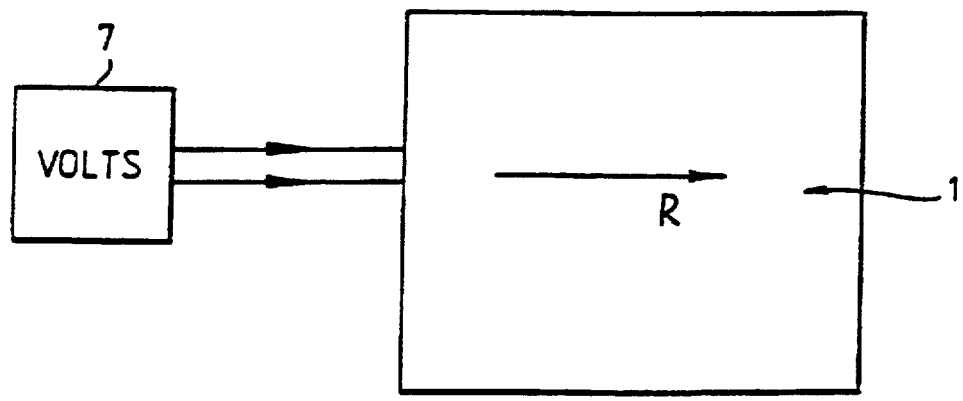
FIGS. 7A and 7B illustrate front and sectional views respectively of a reflective spatial light modulator drawn to different scales, in which the materials of the current invention may be incorporated.
Figure 7B:
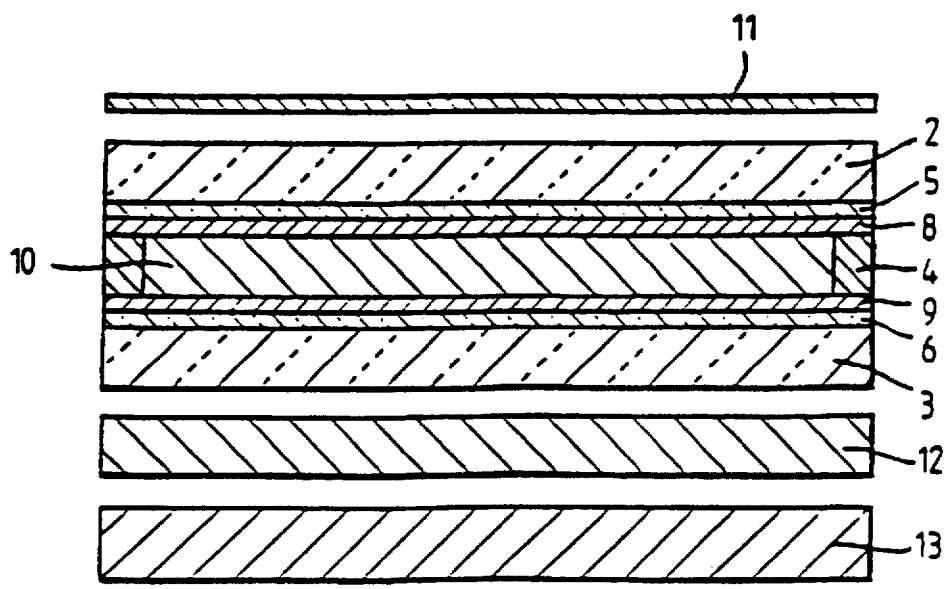

As shown in FIGS. 7A and 7B, a spatial light modulator comprises a liquid crystal cell 1 formed by two glass walls 2, 3 and a 1–10 μm eg 2.5 μm thick spacer 4. The inner faces of the walls carry thin transparent indium tin oxide electrodes 5, 6 connected to a variable voltage source 7. On top of the electrodes 5, 6 are surface alignment layers 8, 9 eg of rubbed polyimide described in more detail later. Other alignment techniques are also suitable eg non-rubbing techniques such as evaporation. A layer 10 of liquid crystal material is contained between the walls 2, 3 and spacer 4. In front of the cell 1 is a linear polariser 11; behind the cell 1 is a quarter plate 12 (this may be optional) and a mirror 13. An example of a linear polariser is a polarising beam splitter (not illustrated here).

The alignment layers 8,9 have two functions one to align contacting liquid crystals molecules in a preferred direction and the other to give a tilt to these molecules—a so called surface tilt—of a few degrees typically around 4° or 5°. The alignment layers 8, 9 may be formed by placing a few drops of the polyimide onto the cell wall and spinning the wall until a uniform thickness is obtained. The polyimide is then cured by heating to a predetermined temperature for a predetermined time followed by unidirectional rubbing (R) (parallel or antiparallel) with a roller coated with a nylon cloth.

There are a variety of electroclinic devices in which the compounds of the present invention may be incorporated. For example in the above description of FIGS. 7A and 7B, active back plane driving may be utilised. One of the walls forming the cell may be formed from a silicon substrate eg a wafer which possesses circuitry for driving pixels. For many of these devices there exists an optimum thickness for the cell which is related to the birefringence ($\Delta n$) given by:

$$d \frac{(2m+1)}{4(\Delta n)} \lambda$$

wherein:

$\lambda$=wavelength of operation $\Delta n$=birefringence of liquid crystalline material m=integer.

Some suitable methods for driving electroclinic devices described by the present invention may be found in UK patent application GB 2 247 972 A.

The mode of operation of the devices described by the current invention includes either amplitude modulation or phase modulation. Similarly, devices may be used in reflectance or transmissive mode.

The following are some example compounds.

EXAMPLE 1

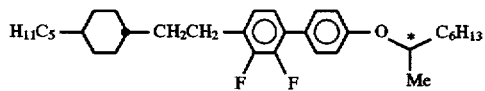

The following compounds are obtained analogously:

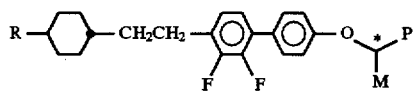

wherein R is selected from $C_{1-12}$ alkyl, M is selected from methyl, ethyl, propyl, butyl or pentyl (including branched chain analogues) and P is selected from $C_{1-12}$ alkyl.

EXAMPLE 2

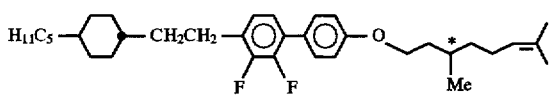

The following compounds are obtained analogously:

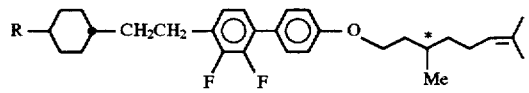

wherein R is selected from $C_{1-12}$ alkyl.

EXAMPLE 3

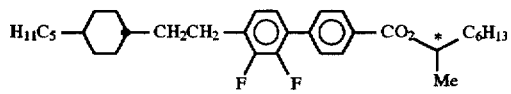

The following compounds are obtained analogously:

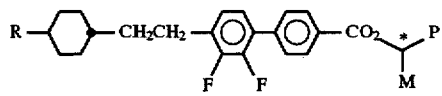

wherein R is selected from $C_{1-12}$ alkyl, M is selected from methyl, ethyl, propyl, butyl or pentyl (including branched chain analogues) and P is selected from $C_{1-12}$ alkyl.

EXAMPLE 4

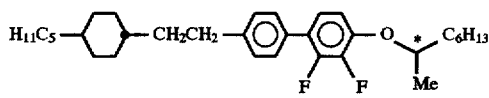

The following compounds are obtained analogously:

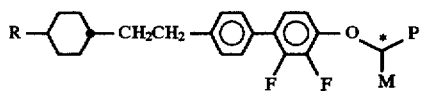

wherein R is selected from $C_{1-12}$ alkyl, M is selected from methyl, ethyl, propyl, butyl or pentyl (including branched chain analogues) and P is selected from $C_{1-12}$ alkyl.

EXAMPLE 5

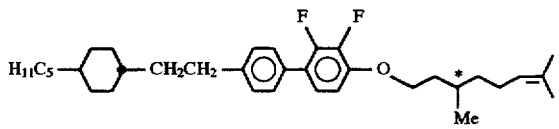

The following compounds are obtained analogously:

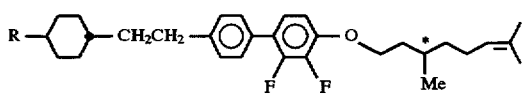

wherein R is selected from $C_{1-12}$ alkyl.

EXAMPLE 6

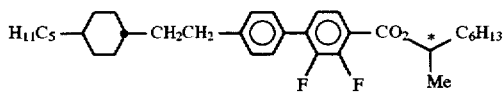

The following compounds are obtained analogously:

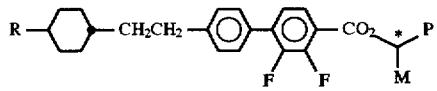

wherein R is selected from $C_{1-12}$ alkyl, M is selected from methyl, ethyl, propyl, butyl or pentyl (including branched chain analogues) and P is selected from $C_{1-12}$ alkyl.

EXAMPLE 7

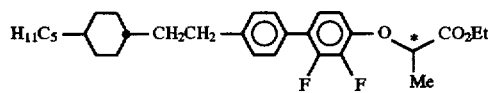

The following compounds are obtained analogously:

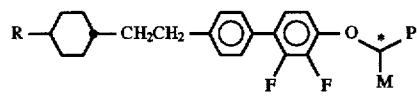

wherein R is selected from $C_{1-12}$ alkyl, M is selected from methyl, ethyl, propyl, butyl or pentyl (including branched chain analogues) and P is $CO_2R_3$ where $R_3$ is selected from $C_{1-6}$ alkyl.

EXAMPLE 8

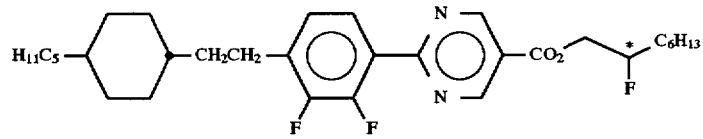

The following compounds are obtained analogously:

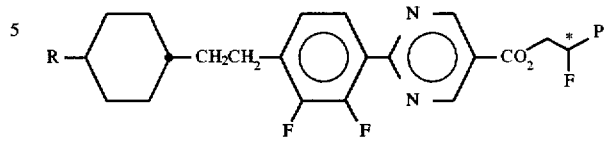

wherein R is selected from $C_{1-12}$ alkyl, P is selected from $C_{1-12}$ alkyl.

EXAMPLE 9

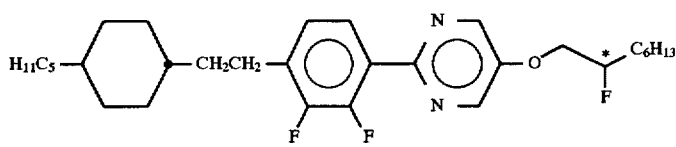

The following compounds are obtained analogously:

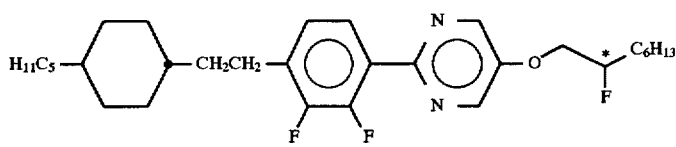

wherein R is selected from $C_{1-12}$ alkyl, P is selected from $C_{1-12}$ alkyl.

EXAMPLE 10

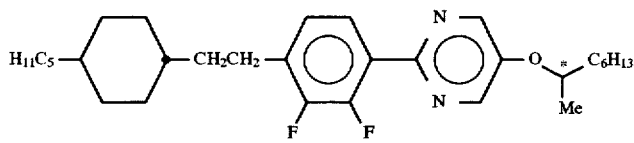

The following compounds are obtained analogously:

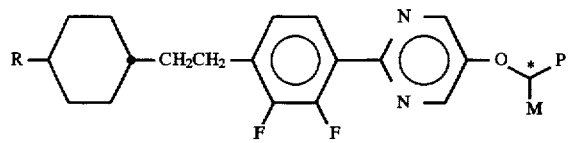

wherein R is selected from $C_{1-12}$ alkyl, P is selected from $C_{1-12}$ alkyl and M is selected from methyl, ethyl, propyl, butyl or pentyl (including branched chain analogues).

Figure 8:
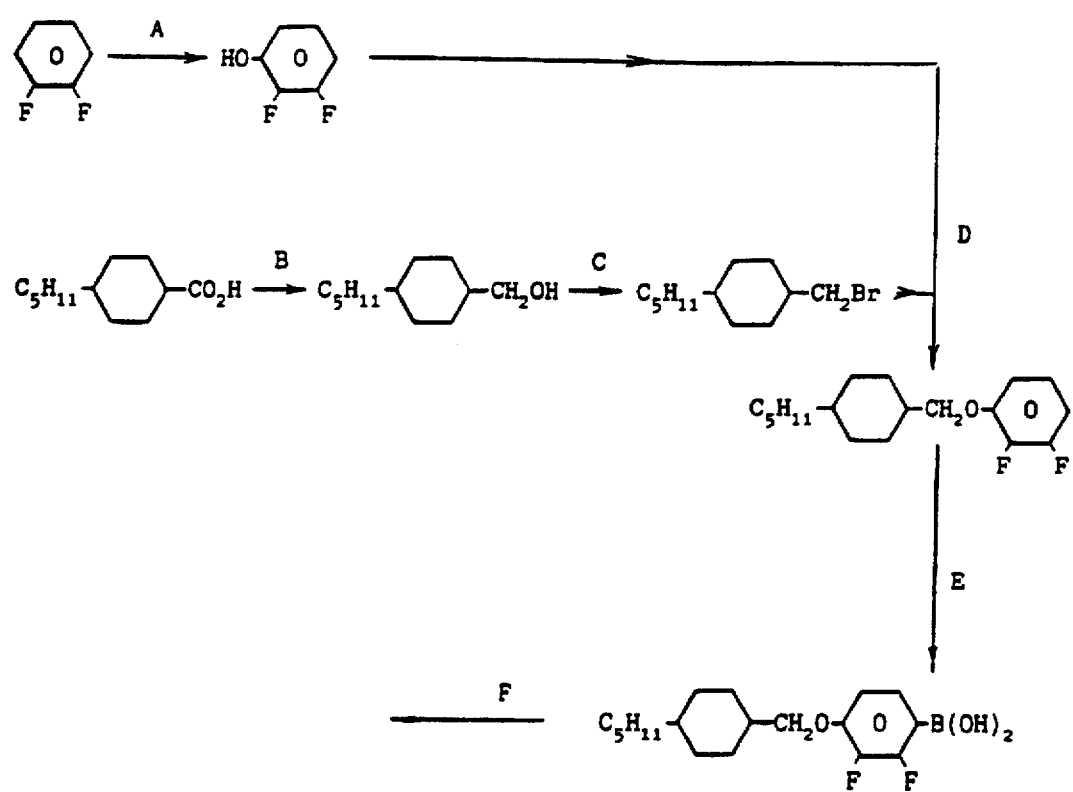
FIG. 8 illustrates a synthetic scheme for the preparation of compounds.

For the above examples and compounds covered by the scope of the present invention, the ethyl bridging group may be replaced with a $CH_2O$ or $OCH_2$ group as illustrated in FIG. 8. The reagents corresponding to FIG. 8 are shown below:

A: (i) BuLi; (ii) $B(OMe)_3$; (iii) HCl; (iv) $H_2O_2$.
B: (i) MeOH, conc $H_2SO_4$; (ii) $LiAlH_4$.
C: $PBr_5$.
D: $K_2CO_3$/acetone.
E: (i) BuLi; (ii) $B(OMe)_3$; (iii) HCl.
F: FIG. 1, Step F onwards.

Table 1 illustrates the phase transition temperatures for the compounds of Formula I; Examples 1–10.

TABLE 1

| Example | Phase Transition Temperature/°C. |
|---|---|
| 1(R) | I 39.7 BP 35.5 Ch |
| (S) | I 38.5 BP 35.1 Ch |
| (ra) | I 39.9 N |
| 2 | I 57.5 $TGB_A$ 56.5 $S_A$ |
| 3 | I 28.7 $S_A$ |
| 5 | I 84.5 Ch 84.3 S |
| 6 | I 46.7 $S_A$ |
| 7 | I 56.5 $S_A$ |
| 8 | I 109.7 BP 109.1 Ch |
| 9 | I 128.6 Ch 99.6 K |
| 10 | I 43.8 Ch 35.3 K |

Transitions obtained from cooling runs on microscopy to –20° C. Figure in parenthesis indicate monotropic transitions. (R) and (S) indicate configuration at chiral centre, (ra) indicates racemate.

It is understood that where the above compounds are optically active, an optically inactive phase can be provided by the same method of synthesis using an optically inactive racemic isomer mixture as starting material. Suitable devices in which the materials of the present invention may be incorporated, include beam steerers, shutters, modulators, and pyroelectric/piezoelectric sensors.

The materials of the present invention may also be useful as dopants in ferroelectric liquid crystals, which may be multiplexed, or they may be used in active backplane ferroelectric liquid crystal systems.

The materials of the current invention may be mixed together and/or with other liquid crystal compounds.

Compounds of formula I may be mixed with a wide range of hosts, for example smectic hosts to form a useful liquid crystal composition. Such compositions can have a range of values of spontaneous polarisation (Ps). Compounds of Formula I may be mixed with one or more of the types of hosts VIII–XIII. These different types of hosts may be mixed together to which the compound of general formula I may also be added.

Typical hosts include:
The compounds described in PCT/GB86/00040, eg of formula VIII

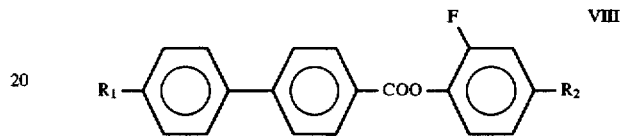

where $R_1$ and $R_2$ are independently $C_3$–$C_{12}$ alkyl or alkoxy. The fluoro-terphenyls described in EPA 84304894.3 and GBA 8725928, eg including those of formula IX

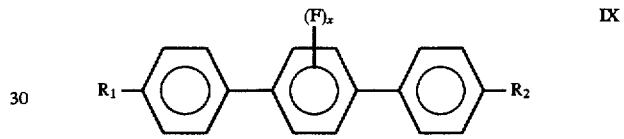

where $R_1$ and $R_2$ are independently $C_3$–$C_{12}$ alkyl or alkoxy, x is 1 and F may be on any of the available substitution positions on the phenyl ring specified.

The difluoro-terphenyls described in GBA 8905422.5, eg of formula X

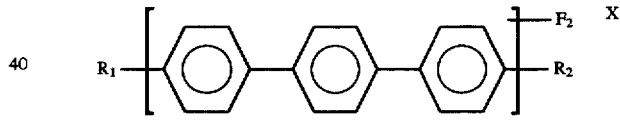

where $R_1$ and $R_2$ are independently $C_3$–$C_{12}$ alkyl or alkoxy. The phenyl-pyrimidines described in WO 86/00087, eg of formula XI

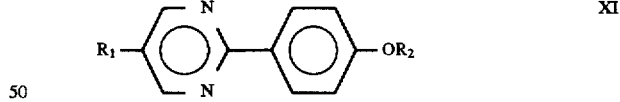

including those compounds where $R_1$ is $C_3$–$C_{12}$ alkyl and $R_2$ is given by the general formula $(CH_2)_n$—$CHXCH_2CH_3$, where n is 1 to 5 and X is CN or Cl.

The compounds described by R. Eidenschink et al. in Cyclohexanederivative mit Getilteneten Smektischen Phasen at the 16$^{th}$ Freiberg Liquid Crystal Conference, Freiberg, Germany, p8. Available from E. Merck Ltd., Germany, eg of formula XII

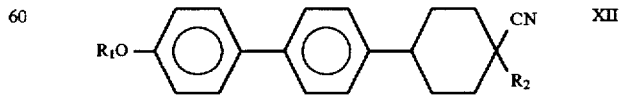

including those compounds where $R_1$ and $R_2$ are independently $C_1$–$C_{15}$ alkyl.

The difluoro-phenyl pyrimidines described at the 2$^{nd}$ International Symposium on Ferroelectric Liquid Crystals, Göteborg, Sweden, June 1989 by Reiffenrath et al., eg of formula XIII

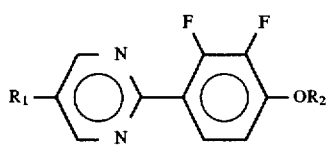

including those compounds where $R_1$ and $R_2$ are independently $C_3$–$C_9$ alkyl. The materials of the present invention may also be useful in thermochromic devices, for example those devices described by D. G. McDonnell in Thermotropic Liquid Crystals, Critical Reports on Applied Chemistry, Vol. 22, edited by G. W. Gray, 1987 pp 120–44 and references therein.

We claim:

1. A compound of Formula I:

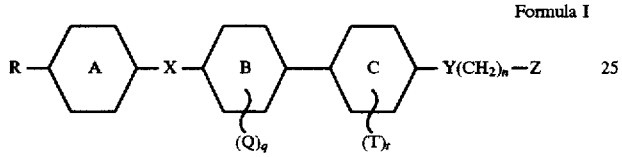

wherein

R is $C_{1-12}$ straight or branched chain alkyl or $C_{2-12}$ alkenyl;

A is cyclohexyl;

X is $CH_2CH_2$

Q and T are independently chosen from fluorine or chlorine and q and t are independently chosen from 0, 1 or 2;

B and C are independently chosen from pyridine, or pyrimidine, or phenyl;

Y is O, COO, OCO or a single bond;

n is 0–5;

Z is given by Formula II and possesses a chiral centre, the chiral carbon is denoted by C in Formula II:

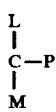

L  
   |  
   C—P  
   |  
   M

Formula II wherein

L is $C_{1-5}$ alkyl or $C_{2-5}$ alkenyl, H, F, CN, $CF_3$, $CHF_2$, $CH_2F$;

M is $C_{1-5}$ alkyl or $C_{2-5}$ alkenyl, or H;

P is H or the group $R_2$ wherein $R_2$ is $C_{1-12}$ branched or straight chain alkyl and may contain a double bond when there is more than one carbon present or P is $CO_2R_3$ where $R_3$ is $C_{1-5}$ alkyl;

provided that there is at least one phenyl ring present.

2. A compound according to claim 1 wherein R is $C_{3-8}$ straight chain alkyl; X is $CH_2CH_2$; B is phenyl; Q is F; C is pyrimidine or phenyl; T is F; Y is O or COO; n=0–2; M=H; L=Me or F; P is $CO_2Et$ or $CH_2\ CH_2\ CHC(CH_3)_2$ or $C_3$–$C_8$ alkyl chain.

3. A liquid crystal device comprising a layer of liquid crystal material contained between two spaced cell walls each bearing electrode structures and surface treated on facing surfaces to align liquid crystal material molecules, characterised in that the liquid crystal material includes the material as described in claim 1.

4. A liquid crystal mixture containing any of the compounds of claim 1 and a host material of the following general formula:

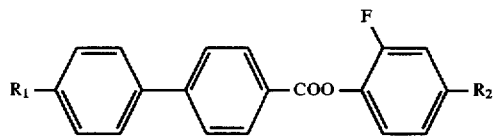

where $R_1$ and $R_2$ are independently $C_3$–$C_{12}$ alkyl or alkoxy.

5. A liquid crystal mixture containing any of the compounds of claim 1 and a host material of the following general formula

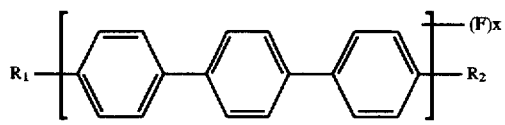

where $R_1$ and $R_2$ are independently $C_3$–$C_{12}$ alkyl or alkoxy, x is 1 and F may be on any one of the available substitution positions on the phenyl rings.

6. A liquid crystal mixture containing any of the compounds of claim 1 and a host material of the following general formula:

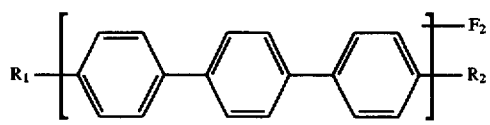

where $R_1$ and $R_2$ are independently $C_3$–$C_{12}$ alkyl or alkoxy.

7. A liquid crystal mixture containing any of the compounds of claim 1 and a host material of the following general formula:

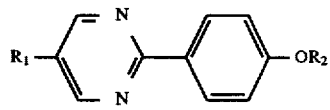

where $R_1$ is $C_3$–$C_{12}$ alkyl and $R_2$ is given by the general formula $(CH_2)_n$–$CHXCH_2CH_3$, where n is 1 to 5 and X is CN or Cl.

8. A liquid crystal mixture containing any of the compounds of claim 1 and a host material of the following general formula:

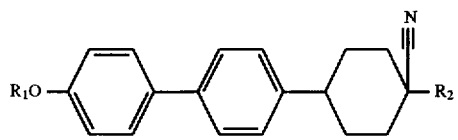

where $R_1$ and $R_2$ are independently $C_1$–$C_{15}$ alkyl or alkoxy.

9. A liquid crystal mixture containing any of the compounds of claim 1 and a host material of the following general formula

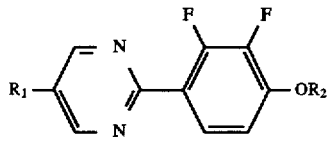

where $R_1$ and $R_2$ are independently $C_3$–$C_9$ alkyl or alkoxy.

10. An electroclinic device comprising two spaced cell walls each bearing electrode structures and treated on at least one facing surface with an alignment layer, a layer of smectic liquid crystal material enclosed between the cell walls, characterised in that the liquid crystal material contains one or more of the compounds described by claim 1.

11. A thermochromic liquid crystal device comprising a layer of cholesteric liquid crystal material contained between two cell walls characterised in that the liquid crystal material contains one or more of the compounds described in claim 1.

12. A device according to claim 11 wherein at least one of the cell walls is surface profiled in a fine grating to align the liquid crystal molecules.

13. A compound according to claim 1 characterised in that the compound is optically active.

14. A liquid crystal material given by one of the formulae:

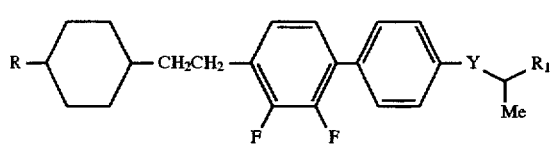

-continued

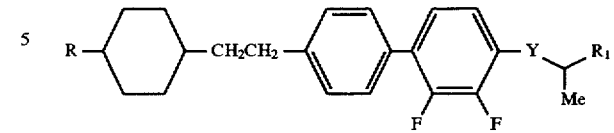

wherein

R is $C_{1-12}$ alkyl;
Y is O or COO;
$R_1$ is $C_{3-8}$ alkyl.

15. A liquid crystal material given by one of the formulae:

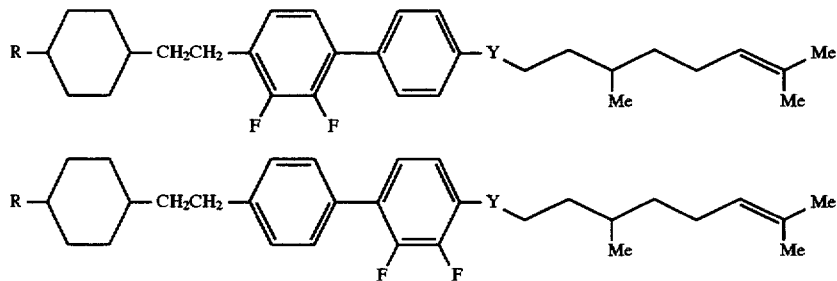

wherein

R is $C_{1-12}$ alkyl;
Y is O or COO.

16. A liquid crystal material given by one of the formulae:

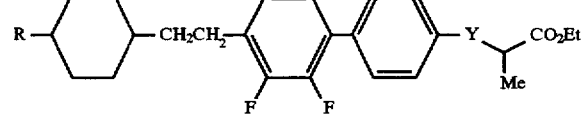

wherein

R is $C_{1-12}$ alkyl;
Y is O or COO.

17. A liquid crystal material given by the formula:

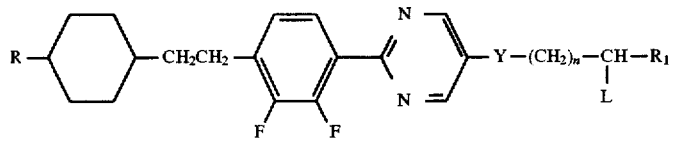
wherein
R=C$_{1-12}$ alkyl;
Y is O or COO;
n=0 or 1;
L=F or Me;
R$_1$=C$_{3-8}$ alkyl.
* * * * *